United States Patent [19]

Irikura

[11] 4,028,370

[45] June 7, 1977

[54] NOVEL PYRAZOLO [1,5-A]PYRIDINES

[75] Inventor: Tsutomu Irikura, Tokyo, Japan

[73] Assignee: Kyorin Pharmaceutical Co., Ltd., Tokyo, Japan

[22] Filed: Oct. 17, 1975

[21] Appl. No.: 623,311

[30] Foreign Application Priority Data

Nov. 1, 1974 Japan .......................... 49-126319

[52] U.S. Cl. .................... 260/296 H; 424/248.54; 424/250; 424/256; 260/247.5 EP; 260/268 BC; 260/294.8 C; 260/294.9; 424/248.57

[51] Int. Cl.² ....................................... C07D 487/00

[58] Field of Search ............................... 260/296 H

Primary Examiner—John D. Randolph
Attorney, Agent, or Firm—Armstrong, Nikaido & Marmelstein

[57] ABSTRACT

The present invention provides substituted pyrazolo[1,5-a]pyridine derivatives expressed by a compound of the general formula (I),

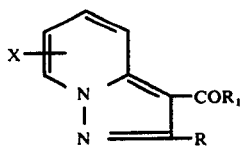

(I)

(wherein: X is hydrogen atom or methyl group; R is hydrogen atom, straight or branched lower alkyl group, lower alkoxy group, lower alkylthio group, dialkylamino group, alkyleneimino group, and morpholino group; $R_1$ is different from R and is hydrogen atom, straight or branched lower alkyl group, lower alkoxy alkyl group, and dialkylamino group).

The compound of the present invention can be prepared by reacting a compound of the general formula (II), (II)

in which X and R are as shown hereinbefore, with a compound of the general formula (III), in which $R_1$ is as shown hereinbefore,

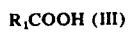

or with a functional derivative of the compound of the general formula (III).

6 Claims, No Drawings

NOVEL PYRAZOLO [1,5-A]PYRIDINES

The compound of the present invention can be prepared by reacting a compound of the general formula (II),

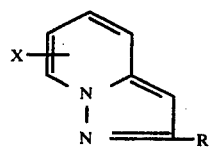

(II)

in which X and R are as shown hereinbefore, with a compound of the general formula (III), in which $R_1$ is as shown hereinbefore,

 (III)

or with a functional derivative of the compound of the general formula (III).

THE DETAILED EXPLANATIONS OF THE PRESENT INVENTION

In the previous patent the present inventor presented 2-alkyl-3-acylpyrazolo[1,5-a]pyridines, in which 2-alkyl group was identical with the alkyl part of 3-acyl radical, having very interesting pharmacological properties of circulatory system (Japanese Kokai Sho No. 48-97898).

Then, the present inventor continued studying on the preparations and physiological properties of the other pyrazolo[1,5-a]pyridine derivatives and found that compounds of the present invention had more useful pharmacological properties than those of the previous patent substance.

Namely, in the present invention, a compound of the general formula (II),

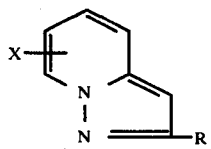

(II)

in which X and R are as shown hereinbefore, may be reacted with a carboxylic acid of the general formula (III), or with a functional derivative of the compound of the general formula (III), in which $R_1$ is as shown hereinbefore,

 (III)

to prepare a compound of this invention having the general formula (I), in which X, R and $R_1$ are as shown hereinbefore,

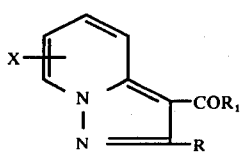

(I)

having very interesting pharmacological properties.

In the compound of the general formula (I) and (II), R may be lower alkyl group such as methyl, ethyl, n-propyl, iso-propyl, n-butyl, iso-butyl, sec-butyl radical and so on, or lower alkoxy group such as, methoxy, ethoxy, propoxy, iso-propoxy radical and so on, or lower alkylthio group such as methylthio, ethylthio, propylthio, iso-propylthio radical and so on, or dialkylamino group such as, dimethylamino, diethylamino, ethylmethylamino radical and so on, or cyclic alkyleneimino group such as, pyrrolidino, piperazino, pipecolino radical and so on.

In the compound of the general formula (I) and (III), $R_1$ may be lower alkyl group such as, methyl, ethyl, n-propyl, iso-propyl, n-butyl, iso-butyl radical and so on, or lower alkoxy alkyl group such as methoxymethyl, ethoxymethyl, 2-ethoxy-1-methylethyl radical and so on, or dialkylamino group such as, dimethylamino radical and so on. A functional derivative of the carboxylic acid of the general formula (III) may be the acid chloride, the acid bromide, the acid anhydride or a mixed-reagent such as acid amido-phosphorus oxychloride, for example, dimethylformamide-phosphorus oxychloride, dimethylacetamide-phosphorus oxychloride, N-methyl-N-phenylacetamide-phosphorus oxychloride and so on, which are known as Vilsmeier reagents.

THE PREPARING PROCEDURE OF THE COMPOUND OF THE PRESENT INVENTION

Namely, a compound of the general formula (II), in the absence of the presence of an inert solvent such as, carbon dilsufide, chloroform, methylene chloride, nitrobenzene and so on, may be reacted with equimolecular or an excess amount of a functional derivative of the compound of the general formula (III), in the range of 0° to the boiling point of a solvent and a reagent used. When the general formula (III) is a carboxylic acid, the presence of a condensing agent such as, phosphorus oxychloride, phosphorus chloride, phosphorus bromide and so on, is preferable. When the general formula (III) is an acid halide, the reaction can be carried out smoothly in the presence or absence of a catalyst such as, aluminum chloride, zinc chloride and so on. When the general formula (III) is a carboxylic anhydride, it is favorable to add a Friedel-Crafts catalyst, and a few drop of concentrated sulfuric acid.

When $R_1$ is hydrogen atom in a compound of the general formula (I), the reaction proceeds satisfactorily by use of a Vilsmeier reagent such as, a mixed reagent of dimethylformamide and phosphorus oxychoride and so on.

Moreover, the starting materials of the general formula (II) in the present invention are new compounds.

When R is alkyl group in a compound of the general formula (II), the compounds are obtained easily by heating the 2-alkyl-3-acylpyrazolo[1,5-a]pyridine derivatives of the previously applied compound (Japanese Kokai Sho No. 48-97898) in acidic conditions such as, in 30–50%(v/v) sulfuric acid.

When R is dialkylamino group in a compound of the general formula (II), the compound is obtained by decyanation in acidic conditions of 3-cyano-2-dialkylaminopyrazolo[1,5-a]pyridine which is obtained by alkylation of 2-amino-3-cyanopyrazolo[1,5-a]pyridine.

When R is alkoxy group is a compound of the general formula (II), the compound is obtained easily by alkylation of 2-hydroxypyrazolo[1,5-a]pyridine with an alkylating agent in the presence of a basic substance.

When R is alkylthio group in a compound of the general formula (II), the compound is obtained from 2-chloropyrazolo[1,5-a]pyridine and an alkali salt of alkyl mercaptane.

The substances of this invention expressed by the general formula (I) have very interesting pharmacological properties, especially such as coronary dilating action (dog), cerebral dilating action (dog), stimulating of cardiac function (dog), hypotensive activity (SHR), and smooth muscle relaxing action (trachea and small intestine).

These properties are useful as a circulatory improver, a hypotensive agent, and an antispasmodic agent.

The effects on blood pressure and coronary flow of pyrazolo[1,5-a]pyridines were examined respectively in spontaneous hypertensive rats (SHR) and isolated guinea pig hearts.

Hypotensive and Coronary Dilating Effects of Novel Pyrazolo[1,5-a]Pyridines

| Ex. No. | KC-No. | Hypotensive Effect* 30 mg/kg (i.p.) | Coronary Flow** 100 μg (i.a.) | | |
|---|---|---|---|---|---|
| 1 | 424 | ++++ | | | |
| 2 | 428 | + | | | |
| 3 | 542 | ++++ | | | |
| 4 | 436 | + | | | |
| 5 | 438 | + | | | |
| 6 | 457 | + | + | | |
| 7 | 543 | +++ | +++ | | |
| 8 | 495 | ++ | ++ | | |
| 9 | 497 | ± | ++ | | |
| 10 | 478 | ++++ | ++ | LD$_{50}$ (mouse) | i.v 188mg/kg p.o 358mg/kg |
| 11 | 589 | ++++ | | | |
| 12 | 590 | ++ | | | |
| 13 | 587 | + | | | |
| 14 | 588 | ++++ | | | |
| 15 | 577 | ± | | | |
| 16 | 578 | ++ | | | |
| 17 | 549 | ++++ | | | |
| Papaverine | | | +++ | | |
| Hexamethonius | | + | | | |
| Guanethidine | | +++ | | | |

*Change in mean blood pressure for 3 hours in unanesthetized spontaneously hypertensive rats (SHR) after oral administration of pyrazolo[1,5-a]pyridines
Percent of control
± : 95 – 105(%)  + : 90 – 95(%)  ++: 85 – 90(%)
+++: 80 – 85(%)  ++++ : – 80(%)
**Increasing ratio of coronary flow in isolated guinea pig hearts after intra arterial injection of pyrazolo[1,5-a]pyridines
+ : 5 – 30(%)  ++ : 30 – 60(%)  +++ : 60 –(%)

Almost all of analogues of pyrazolo[1,5-a]pyridines showed a marked hypotensive action and a coronary dilating effect. For example, the compounds No. 1, 3, 10, 11, 14 and 17 decreased markedly the blood pressure in SHR, and No. 7, 8, 9 and 10 increased the coronary flow in isolated guinea pig hearts.

From these results, the substances of this invention are recognized to be useful as hypotensive and/or coronary vasodilating agents.

For purpose of illustration only, this invention will now be illustrated by the following examples. Of course, this invention should not be limited to the following examples.

EXAMPLE 1 FOR REFERENCE

Synthesis of 2-isopropylpyrazolo[1,5-a]pyridine

A mixture of 30g (0.13 mole) of 2-isopropyl-3-isobutyrylpyrazolo[1,5-a]pyridine and 200 ml of 50% sulfuric acid (v/v) solution was heated at 140° C for 10 hours. After cooling, the mixture was added to 400g of ice-water. The solution was neutralized with sodium hydroxide solution and extracted with chloroform. The chloroform solution was dried over anhydrous sodium sulfate and concentrated under reduced pressure. The residue was distilled to give 8.5g (5.3 × 10$^{-2}$ mole) of colorless oily product, bp 127.5°–129.5° C (17 mmHg).

EXAMPLE 2 FOR REFERENCE

Synthesis of 2-dimethylaminopyrazolo[1,5-a]pyridine

A mixture of 3.25g (1.6 × 10$^{-2}$ mole) of 3-carbamoyl-2-dimethylaminopyrazolo[1,5-a]pyridine and 100 ml of concentrated hydrochloric acid was refluxed for 5 hours. After cooling, the solution was made to alkali and extracted with chloroform. The chloroform solution was dried over sodium sulfate and concentrated. The residue was column-chromatographed over alumina. The elution with methylene chloride gave crude product, which was recrystallized from n-hexane to give 1.3g of colorless needles, mp 51°–52° C. Yield 50%.

EXAMPLE 3 FOR REFERENCE

Synthesis of 2-methoxypyrazolo[1,5-a]pyridine

Sodium (92 mg) was dissolved in 5 ml of absolute methyl alcohol with moderate cooling. To this solution 2-hydroxypyrazolo[1,5-a]pyridine (500 mg) was added and then dimethyl sulfate (500 mg) was added. The mixture was stirred for 30 min. at room temperature and refluxed for 8 hr. The reaction mixture was concentrated to remove methyl alcohol, and water was added to the residue. The solution was extracted with n-hexane, and the n-hexane solution was dried over sodium sulfate. The dried n-hexane solution was concentrated and the residue was distilled to give 280 mg of oily product under reduced pressure.

EXAMPLE 1

Synthesis of 3-acetyl-2-isopropylpyrazolo[1,5-a]pyridine (KC-424)

A mixture of 4.2g of 2-isopropylpyrazolo[1,5-a]pyridine, 10.2g of acetic anhydride and 2–3 drops of concentrated sulfuric acid was refluxed for 7 hr. After cooling, the mixture was added to 200 ml of 4M potassium hydroxide solution and stirred for 1 hr. The solution was extracted with chloroform and the chloroform solution was dried over sodium sulfate. The dried chloroform solution was concentrated and the residue was column-chromatographed over alumina to isolate objective product. Recrystallization from n-hexane gave 4.3g of colorless needles, mp 74° C. Yield 67%.

EXAMPLE 2

Synthesis of 3-acetyl-2-n-propylpyrazolo[1,5-a]pyridine (KC-428)

2-n-Propylpyrazolo[1,5-a]pyridine (4.8g) was worked up according to the same process as shown in example 1, with acetic anhydride (10.2g) and 2–3 drops of concentrated sulfuric acid to prepare the objective product of colorless prisms, mp 98°–99°. Yield 4g (63%).

EXAMPLE 3

Synthesis of 2-isopropyl-3-propionylpyrazolo[1,5-a]pyridine (KC-542)

2-Isopropylpyrazolo[1,5-a]pyridine was worked up according to same process as shown in example 1, with propionic anhydride in the presence of 2–3 drops of concentrated sulfuric acid. The same procedure as that in example 1 afforded an oily product, bp 162°–166° (7 mmHg), which crystallized afterwards. Recrystallization from n-hexane gave colorless needles, mp 41°–42°. Yield 39%.

EXAMPLE 4

Synthesis of the 3-formyl-2-isopropylpyrazolo[1,5-a]pyridine (KC-436)

One gram of 2-isopropylpyrazolo[1,5-a]pyridine was dissolved in 0.6 ml of dimethylformamide, and 5 ml of phosphorus oxychloride was added to the resulting solution. The reaction mixture was refluxed for 20 min., poured into ice-water, and neutralized with potassium carbonate. The precipitate was collected by filtration and washed with water. Recrystallization from n-hexane gave 800 mg of colorless needles, mp 81.0°–81.5°. Yield 67%.

EXAMPLE 5

Synthesis of 3-acetyl-2-isobutylpyrazolo[1,5-a]pyridine (KC-438)

2-Isobutylpyrazolo[1,5-a]pyridine was worked up according to same process as shown in example 1, with an excess acetic anhydride in the presence of a few drops of concentrated sulfuric acid, to prepare 3-acetyl-2-isobutylpyrazolo[1,5-a]pyridine (bp 165°–168°/7mmHg). Yield 79%.

EXAMPLE 6

Synthesis of 3-acetylpyrazolo[1,5-a]pyridine (KC-457)

Pyrazolo[1,5-a]pyridine was worked up according to the same process as shown in example 1, with an excess acetic anhydride in the presence of a few drops of concentrated sulfuric acid to prepare 3-acetylpyrazolo[1,5-a]pyridine. The product was column chromatographed over alumina with benzene as an eluent to purify the objective product. Recrystallization from benzene gave colorless needles, mp 96°–97°. Yield 42%.

EXAMPLE 7

Synthesis of 3-isobutyryl-2-methylpyrazolo[1,5-a]pyridine (KC-543)

2-Methylpyrazolo[1,5-a]pyridine was worked up according to the same process as shown in example 1, with an excess isobutyric anhydride in the presence of 2–3 drops of concentrated sulfuric acid to prepare 3-isobutyryl-2-methylpyrazolo[1,5-a]pyridine (139°–140°/5 mmHg). Yield 40%.

EXAMPLE 8

Synthesis of 3-acetyl-2-isopropyl-7-methylpyrazolo[1,5-a]pyridine (KC-495)

2-Isopropyl-7-methylpyrazolo[1,5-a]pyridine was worked up according to the same process as shown in example 1, with an excess acetic anhydride in the presence of a few drops of concentrated sulfuric acid to prepare 3-acetyl-2-isopropyl-7-methylpyrazolo[1,5-a]pyridine (147°–148°/4 mmHg). Recrystallization from n-hexane gave colorless prisms, mp 67.5°–68.0°. Yield 52%.

EXAMPLE 9

Synthesis of 3-acetyl-2-isopropyl-4-methylpyrazolo[1,5-a]pyridine (KC-497)

2-Isopropyl-4-methylpyrazolo[1,5-a]pyridine was worked up according to the same process as shown in example 1, with an excess acetic anhydride in the presence of a few drops of concentrated sulfuric acid to prepare 3-acetyl-2-isopropyl-4-methylpyrazolo[1,5-a]pyridine. The product was column chromatographed over alumina to purify the objective product. Recrystallization from ethyl alcohol gave colorless prisms, mp 71°–72°. Yield 65%.

EXAMPLE 10

Synthesis of 3-acetyl-2-dimethylaminopyrazolo[1,5-a]pyridine (KC-478)

A mixture of 2.3g of 2-dimethylaminopyrazolo[1,5-a]pyridine and 30 ml of acetic anhydride in the presence of concentrated sulfuric acid was refluxed for 2.5 hr. After cooling, the mixture was poured into ice water. The solution was neutralized with potassium carbonate and extracted with chloroform. The chloroform solution was dried over sodium sulfate and concentrated. The residue was column chromatographed over alumina to purify the objective product. Recrystallization from n-hexane gave colorless prisms, mp 80.5°–81.5°. Yield 700 mg.

EXAMPLE 11

Synthesis of 3-acetyl-2-pyrrolidinopyrazolo[1,5-a]pyridine (KC-589)

2-Pyrrolidinopyrazolo[1,5-a]pyridine was worked up according to the same process as shown in example 10, to prepare the objective product, which was recrystallized from n-hexane to give colorless needles, mp 59.5°–60.0°.

EXAMPLE 12

Synthesis of 3-acetyl-2-morpholinopyrazolo[1,5-a]pyridine (KC-590)

2-Morpholinopyrazolo[1,5-a]pyridine was worked up according to the same process as shown in example 10, to prepare the objective product which was recrystallized from n-hexane-ethyl acetate to give colorless prisms, mp 164°.

EXAMPLE 13

Synthesis of 3-acetyl-2-methoxypyrazolo[1,5-a]pyridine (KC-587)

A mixture of 2-methoxypyrazolo[1,5-a]pyridine (280 mg) acetic anhydride (3 ml) and acetyl chloride (1 ml) was refluxed for 1 hr and the reaction mixture was concentrated under reduced pressure. Water was added to the residue and the solution was made basic with potassium carbonate. The precipitated crystals were collected and washed with water. Recrystallization from n-hexane-ethyl acetate gave colorless needles, mp 158.0°–158.5°. Yield 160 mg.

EXAMPLE 14

Synthesis of 3-acetyl-2-ethylthiopyrazolo[1,5-a]pyridine (KC-588)

2-Ethylthiopyrazolo[1,5-a]pyridine was worked up according to the same process as shown in example 13, to prepare 3-acetyl-2-ethylthiopyrazolo[1,5-a]pyridine which was recrystallized from n-hexane to give colorless needles, mp 84°–85°.

EXAMPLE 15

Synthesis of 3-(N,N-dimethylcarbamoyl)-2-methylpyrazolo[1,5-a]pyridine (KC-577)

2-Methylpyrazolo[1,5-a]pyridine (3.6g) was dissolved in N,N-dimethylcarbamoyl chloride (10.8g). Aluminum chloride (8.0g) was added to the resulting solution and the mixture was heated at 130° for 3 hr and poured into ice water. The solution was made basic with potassium hydroxied solution and extracted with chloroform. The chloroform solution was dried over sodium sulfate and concentrated. The residue was distilled to give 1.8g of the objective product, bp 149°–150° (2 mmHg). Yield 32%.

EXAMPLE 16

Synthesis of 3-(N,N-dimethylcarbamoyl)-2-isopropylpyrazolo[1,5-a]pyridine (KC-578)

A mixture of 1.6g of 2-isopropylpyrazolo[1,5-a]pyridine and 2.1g of N,N-dimethylcarbamoyl chloride was dissolved in 20 ml of nitrobenzene. Four grams of aluminum chloride (powder) was added at room-temperature to the resulting solution and reaction mixture was refluxed for 8 hr and concentrated under reduced pressure. Water was added to the residue and the mixture was made basic with potassium hydroxide solution, extracted with chloroform. The chloroform solution was dried over sodium sulfate and concentrated. The residue was column chromatographed over aluminum to give objective product. Distillation gave colorless oil, bp 175° (2 mmHg). Yield 1.1g (50%).

EXAMPLE 17

Synthesis of 3-(β-ethoxy-α-methylpropionyl)-2-isopropyl-pyrazolo[1,5-a]pyridine (KC-549)

A mixture of 2-isopropylpyrazolo[1,5-a]pyridine and β-ethoxy-α-methylpropionic chloride was dissolved in carbon disulfide. Aluminum chloride was added at 0° to the resulting solution. The reaction mixture was stirred for 3 hr, and poured into water. The solution was made basic with potassium hydroxide solution and extracted with chloroform. The chloroform solution was washed with water, dried over sodium sulfate and concentrated. The residue was distilled, bp 171°–173° (4 mmHg). Yield 32%.

EXAMPLE 18

Synthesis of 3-acetyl-2-dimethylaminopyrazolo[1,5-a]pyridine (KC-478)

To a solution of 68g of 2-dimethylaminopyrazolo[1,5-a]pyridine in 300 ml of pyridine was added dropwise 300 ml of acetic anhydride under cooling and stirring. The mixture was refluxed for 7 hr. and then concentrated. The residue was poured into ice-water (900g) and the solution was extracted three times with benzene (300 ml). The benzene layer was washed with water (300 ml) and dried over anhydrous potassium carbonate. The solution was concentrated under reduced pressure and the residue was distilled under reduced pressure (bp 130°–150°/0.25 mmHg) to obtain 60g of the objective product, which was recrystallized from n-hexane-benzene (20:1) to give 42g of colorless prisms, mp 78°–80.5°.

Analysis: Calcd: C, 65.00; H, 6.45; N, 20.78. Found: C, 65.07; H, 6.43; N, 20.78.

The compound thus obtained was identical with that prepared in example 10.

EXAMPLE 19

Synthesis of 3-acetyl-2-dimethylaminopyrazolo[1,5-a]pyridine (KC-616)

2-Diethylaminopyrazolo[1,5-a]pyridine (500 mg) was worked up according to the same process as shown in example 18, to prepare the objective product, which was recrystallized from n-hexane to give colorless prisms (350 mg), mp 59.5°–60.0°.

Analysis: Calcd: C, 67.50; H, 7.41; N, 18.17. Found: C, 67.64; H, 7.45; N, 18.21.

EXAMPLE 20

Synthesis of 2-dimethylamino-3-propionylpyrazolo[1,5-a]pyridine (KC-617)

2-Dimethylaminopyrazolo[1,5-a]pyridine (300 mg) was worked up according to the same process as shown in example 18, with propionic anhydride (2 ml) and pyridine (1.5 ml) to prepare the objective product of colorless oil (200 mg: bp 103°–115°/0.05 mmHg).

Analysis: Calcd. for its picrate (mp 139°–140°, yellow prisms from EtOH): C, 48.43; H, 4.06; N, 18.83. Found: C, 41.36; H, 4.03; N, 18.32.

EXAMPLE 21

Synthesis of 2-dimethylamino-3-isobutyrylpyrazolo[1,5-a]pyridine (KC-618)

2-Dimethylaminopyrazolo[1,5-a]pyridine (150 mg) was worked up according to the same process as shown in example 18, with isobutyric anhydride (1 ml) and pyridine (1 ml) to prepare the objective product of colorless oil (60 mg).

What is claimed is:

1. A compound of the general formula:

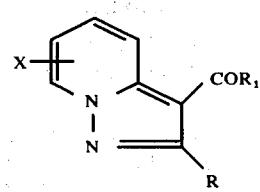

wherein X is hydrogen or methyl; R is dialkylamino or alkyleneimino; and $R_1$ is different from R and is hydrogen, straight or branched lower alkyl, or lower alkoxy alkyl.

2. 3-Acetyl-2-dimethylaminopyrazolo[1,5-a]pyridine.
3. 3-Acetyl-2-pyrrolidinopyrazolo[1,5-a]pyridine.
4. 3-Acetyl-2-diethylaminopyrazolo[1,5-a]pyridine.
5. 2-Dimethylamino-3-propionylpyrazolo[1,5-a]pyridine.
6. 2-Dimethylamino-3-isobutyrylpyrazolo[1,5-a]pyridine.

* * * * *